(12) United States Patent
Gadewar et al.

(10) Patent No.: US 8,449,849 B2
(45) Date of Patent: May 28, 2013

(54) CONTINUOUS PROCESS FOR CONVERTING NATURAL GAS TO LIQUID HYDROCARBONS

(75) Inventors: Sagar B. Gadewar, Goleta, CA (US); Michael D. Wyrsta, Santa Barbara, CA (US); Philip Grosso, Auburn, CA (US); Aihua Zhang, Santa Barbara, CA (US); Eric W. McFarland, Santa Barbara, CA (US); Zachary J. A. Komon, Goleta, CA (US); Jeffrey H. Sherman, Sebastian, FL (US)

(73) Assignee: GRT, Inc., Santa Barbara, CA (US)

(*) Notice: Subject to any disclaimer, the term of this patent is extended or adjusted under 35 U.S.C. 154(b) by 0 days.

(21) Appl. No.: 13/242,616

(22) Filed: Sep. 23, 2011

(65) Prior Publication Data
US 2012/0009090 A1    Jan. 12, 2012

Related U.S. Application Data

(60) Division of application No. 12/496,348, filed on Jul. 1, 2009, now Pat. No. 8,053,616, which is a continuation of application No. 11/703,358, filed on Feb. 5, 2007, now Pat. No. 7,579,510.

(60) Provisional application No. 60/765,115, filed on Feb. 3, 2006.

(51) Int. Cl.
*B01J 8/04* (2006.01)
*B01J 8/00* (2006.01)
*B01J 10/00* (2006.01)
*B01J 19/00* (2006.01)
*C07C 2/00* (2006.01)
*C07C 4/00* (2006.01)
*C07C 5/00* (2006.01)

(52) U.S. Cl.
USPC ........... 422/630; 422/129; 422/187; 422/600; 585/310; 585/500

(58) Field of Classification Search
USPC ................. 422/129, 600, 630, 187; 585/310, 585/500, 638, 641, 642; 568/300, 420, 448, 568/449, 490
See application file for complete search history.

(56) References Cited

U.S. PATENT DOCUMENTS

| | | | |
|---|---|---|---|
| 3,894,927 A | | 7/1975 | Kane et al. |
| 3,976,447 A | | 8/1976 | Merchant et al. |
| 4,654,449 A | * | 3/1987 | Chang et al. ........... 570/261 |
| 5,087,786 A | * | 2/1992 | Nubel et al. ........... 585/500 |

(Continued)

OTHER PUBLICATIONS

International Search Report for PCT/US09/50955 dated Nov. 2, 2009.

(Continued)

*Primary Examiner* — Jill Warden
*Assistant Examiner* — Natasha Young
(74) *Attorney, Agent, or Firm* — Adolph Locklar

(57) ABSTRACT

A method comprising providing a halogen stream; providing a first alkane stream; reacting at least a portion of the halogen stream with at least a portion of the first alkane stream to form a halogenated stream, wherein the halogenated stream comprises alkyl monohalides, alkyl polyhalides, and a hydrogen halide; providing a second alkane stream; and reacting at least a portion of the second alkane stream with at least a portion of the alkyl polyhalides to create at least some additional alkyl monohalides.

12 Claims, 8 Drawing Sheets

U.S. PATENT DOCUMENTS

| | | | |
|---|---|---|---|
| 5,919,994 A * | 7/1999 | Rao | 570/176 |
| 6,053,007 A | 4/2000 | Victory et al. | |
| 8,053,616 B2 | 11/2011 | Gadewar et al. | |
| 2004/0006246 A1 * | 1/2004 | Sherman et al. | 568/470 |
| 2005/0171393 A1 * | 8/2005 | Lorkovic | 585/357 |
| 2005/0192468 A1 * | 9/2005 | Sherman et al. | 570/102 |
| 2005/0222475 A1 * | 10/2005 | Duplan et al. | 585/329 |
| 2006/0025643 A1 * | 2/2006 | Rath et al. | 585/522 |
| 2007/0251382 A1 | 11/2007 | Gadewar | |
| 2008/0269534 A1 | 10/2008 | Lorkovic | |
| 2008/0314758 A1 | 12/2008 | Grosso | |
| 2009/0069606 A1 | 3/2009 | Komon | |
| 2009/0127163 A1 | 5/2009 | Weiss | |
| 2010/0009993 A1 | 1/2010 | Wang et al. | |
| 2010/0096588 A1 | 4/2010 | Gadewar | |
| 2010/0099928 A1 | 4/2010 | Gadewar | |
| 2010/0099929 A1 | 4/2010 | Gadewar | |
| 2010/0105972 A1 | 4/2010 | Lorkovic | |
| 2010/0121119 A1 | 5/2010 | Sherman | |

OTHER PUBLICATIONS

International Search Report for PCT/US07/03091 dated Jun. 7, 2008.
Office Action from U.S. Appl. No. 12/504,865 dated Feb. 9, 2012.
Office Action from U.S. Appl. No. 12/504,865 dated Oct. 7, 2011.
Office Action from U.S. Appl. No. 12/504,865 dated Jan. 3, 2012.
Office Action from U.S. Appl. No. 12/504,880 dated Mar. 2, 2012.
Office Action from U.S. Appl. No. 12/504,894 dated Jul. 19, 2011.
Office Action from U.S. Appl. No. 12/504,894 dated Apr. 1, 2011.
Communication from New Zealand Intellectual Property Office regarding Application No. 588129 dated Feb. 9, 2012.
Communication from New Zealand Intellectual Property Office regarding Application No. 588129 dated Sep. 29, 2010.
Communication from New Zealand Intellectual Property Office regarding Application No. 591207 dated Jun. 10, 2011.
Communication from European Patent Office regarding Application No. 07749992.9 dated Jun. 9, 2011.

* cited by examiner

CONTINUOUS PROCESS FOR CONVERTING NATURAL GAS TO LIQUID HYDROCARBONS

CROSS-REFERENCE TO RELATED APPLICATION

This application is a divisional of U.S. patent application Ser. No. 12/496,348, filed Jul. 1, 2009, which is a continuation of U.S. patent application Ser. No. 11/703,358, filed Feb. 5, 2007 and issued as U.S. Pat. No. 7,579,510 on Aug. 25, 2009, which claims priority to U.S. Provisional Patent Application No. 60/765,115, filed Feb. 3, 2006. The entire contents of each are incorporated by reference herein.

BACKGROUND OF THE INVENTION

This invention generally relates to carbon-carbon coupling and, more particularly, to methods for converting hydrocarbon feedstocks into useful products.

Scientists have long sought efficient ways to convert methane and other hydrocarbons into longer chain hydrocarbons, olefins, aromatic hydrocarbons, and other products. CH bond activation has been the focus of intense research for decades, with mixed results. More efficient processes could create value in a number of ways, including facilitating the utilization of remotely located hydrocarbon feedstocks (such as stranded natural gas) through conversion into more easily transportable and useful fuels and feedstocks, and allowing the use of inexpensive feedstocks (e.g., methane and other light hydrocarbons) for end products often made from higher hydrocarbons.

U.S. Pat. No. 6,525,230 discloses methods of converting alkanes to other compounds using a "zone reactor" comprised of a hollow, unsegregated interior defining first, second, and third zones. Oxygen reacts with metal bromide in the first zone to provide bromine; bromine reacts with the alkane in the second zone to form alkyl bromide and hydrogen bromide; and the alkyl bromide reacts with metal oxide in the third zone to form the corresponding product. In one embodiment, the flow of gases through the reactor is reversed to convert the metal oxide back to metal bromide and to convert the metal bromide back to the metal oxide. The reactor is essentially operated in a cyclic mode.

U.S. Pat. No. 6,452,058 discloses an oxidative halogenation process for producing alkyl halides from an alkane, hydrogen halide, and, preferably, oxygen, using a rare earth halide or oxyhalide catalyst. The alternative of using molecular halogen is also mentioned. Other patents, such as U.S. Pat. Nos. 3,172,915, 3,657,367, 4,769,504, and 4,795,843, disclose the use of metal halide catalysts for oxidative halogenation of alkanes. Oxidative halogenation, however, has several disadvantages, including the production of perhalogenated products and an unacceptable quantity of deep oxidation products ($CO$ and $CO_2$).

Three published U.S. patent applications, Pub. Nos. 2005/0234276, 2005/0234277, and 2006/0100469 (each to Waycuilis), describe bromine-based processes for converting gaseous alkanes to liquid hydrocarbons. Several basic steps are described, including (1) reacting bromine with alkanes to produce alkyl bromides and hydrobromic acid (bromination), (2) reacting the alkyl bromide and hydrobromic acid product with a crystalline alumino-silicate catalyst to form higher molecular weight hydrocarbons and hydrobromic acid (coupling), (3) neutralizing the hydrobromic acid by reaction with an aqueous solution of partially oxidized metal bromide salts (as metal oxides/oxybromides/bromides) to produce a metal bromide salt and water in an aqueous solution, or by reaction of the hydrobromic acid with air over a metal bromide catalyst, and (4) regenerating bromine by reaction of the metal bromide salt with oxygen to yield bromine and an oxidized salt. Potential drawbacks of the processes include low methane conversions; short space-times and the resulting potential for less than 100% bromine conversion; wasteful overbromination of ethane, propane, and higher alkanes, resulting in the formation of dibromomethane and other polybrominated alkanes, which will likely form coke under the disclosed reaction conditions; comparatively low alkyl bromide conversions; the need to separate the hydrocarbon product stream from an aqueous hydrohalic acid stream; and inadequate capture of halogen during the regeneration of the catalyst to remove halogen-containing coke. In addition, the proposed venting of this bromine-containing stream is both economically and environmentally unacceptable.

The Waycuilis process also apparently requires operation at relatively low temperatures to prevent significant selectivity to methane. The likely result would be incomplete conversion of alkyl bromide species and, because the described process relies on stream splitting to recover products, a considerable amount of unconverted alkyl bromides would likely leave the process with the products. This represents an unacceptable loss of bromine (as unconverted methyl bromide) and a reduced carbon efficiency.

The neutralization of hydrobromic acid by reaction with an aqueous solution of partially oxidized metal bromide salts and subsequent reaction of the metal bromide salts formed with oxygen to yield bromine and an oxidized salt, as disclosed by Waycuilis, also has a number of disadvantages. First, any carbon dioxide present will form carbonates in the slurry, which will not be regenerable. Second, the maximum temperature is limited due to pressure increases which are intolerable above approximately $200°$ C., thus preventing complete recovery of halogen. Third, although the use of redox-active metal oxides (e.g., oxides of V, Cr, Mn, Fe, Co, Ce, and Cu) will contribute to molecular bromine formation during the neutralization of hydrobromic acid, incomplete HBr conversion due to the use of a solid bromide salt will in turn result in a significant loss of bromine from the system (in the water phase). Provided an excess of air was used, the bromide salt might eventually be converted to the oxide form, stopping any further loss of HBr in the water discard.

To separate water from bromine, Waycuilis discloses the use of condensation and phase separation to produce semi-dry liquid bromine and a water/bromine mixture. Other means for separating water from bromine, such as using an inert gas to strip the bromine from the water phase or using adsorption-based methods have also been proposed by others; however, such methods are minimally effective and result in a significant overall loss of halogen.

The prior art oxychlorination process first removes the water from HCl (a costly step) and then reacts the HCl with oxygen and hydrocarbon directly. Oxychlorination processes rely on the separation of HCl from the unreacted alkanes and higher hydrocarbon products by using water absorption, and subsequent recovery of anhydrous HCl from the aqueous hydrochloric acid. U.S. Pat. No. 2,220,570 discloses a process and apparatus for the absorption of HCl in water where the heat of absorption is dissipated by contacting the HCl gas with ambient air, and also by the vaporization of water. A process for producing aqueous hydrochloric acid with a concentration of at least 35.5 wt % by absorbing gaseous HCl in water is disclosed in U.S. Pat. No. 4,488,884. U.S. Pat. No. 3,779,870 teaches a process for the recovery of anhydrous HCl gas by extractive distillation using a chloride salt. U.S.

Pat. No. 4,259,309 teaches a method for producing gaseous HCl from dilute aqueous HCl using an amine together with an inert water-immiscible solvent.

Although researchers have made some progress in the search for more efficient CH bond activation pathways for converting natural gas and other hydrocarbon feedstocks into fuels and other products, there remains a tremendous need for a continuous, economically viable, and more efficient process.

SUMMARY OF THE INVENTION

This invention generally relates to carbon-carbon coupling and, more particularly, to methods for converting hydrocarbon feedstocks into useful products.

An embodiment provides a method comprising providing a halogen stream; providing a first alkane stream; reacting at least a portion of the halogen stream with at least a portion of the first alkane stream to form a halogenated stream, wherein the halogenated stream comprises alkyl monohalides, alkyl polyhalides, and a hydrogen halide; providing a second alkane stream; and reacting at least a portion of the second alkane stream with at least a portion of the alkyl polyhalides to create at least some additional alkyl monohalides.

Another embodiment provides a system for forming hydrocarbons comprising a halogenation reactor, wherein the halogenation reactor receives a quantity of halide and a first quantity of alkane and produces a halogenated product; a reproportionation reactor, wherein the reproportionation reactor receives the halogenated product and a second quantity of alkane and produces at least some alkyl monohalide product and a quantity of hydrogen halide; and a oligomerization reactor comprising a catalyst, wherein the oligomerization reactor receives alkyl monohalide and produces a quantity of hydrocarbon product and a second quantity of hydrogen halide.

Yet another embodiment provides a method comprising providing an alkyl halide stream comprising alkyl monohalides, alkyl polyhalides, and a hydrogen halide; providing a first alkane stream; reacting at least a portion of the first alkane stream with at least a portion of the alkyl halide stream to create at least some additional alkyl monohalides; contacting at least some of the alkyl monohalides and at least some of the additional alkyl monohalides with a catalyst to form a product stream that comprises higher hydrocarbons, hydrogen halide, and any unreacted portion of the first alkane stream; separating the unreacted portion of the first alkane stream from the product stream; providing a halogen stream; and reacting at least some of the unreacted portion of the first alkane stream separated from the product stream with the halogen to form the alkyl halide stream.

Still another embodiment provides a method comprising providing an alkyl halide stream; contacting at least some of the alkyl halides with a catalyst to form a product stream that comprises higher hydrocarbons and hydrogen halide; separating the hydrogen halide from the product stream; and reacting the hydrogen halide with a source of oxygen in the presence of a cerium oxide catalyst to generate a corresponding halogen.

The features and advantages of the present invention will be apparent to those skilled in the art. While numerous changes may be made by those skilled in the art, such changes are within the spirit of the invention.

DETAILED DESCRIPTION

Figure 1:
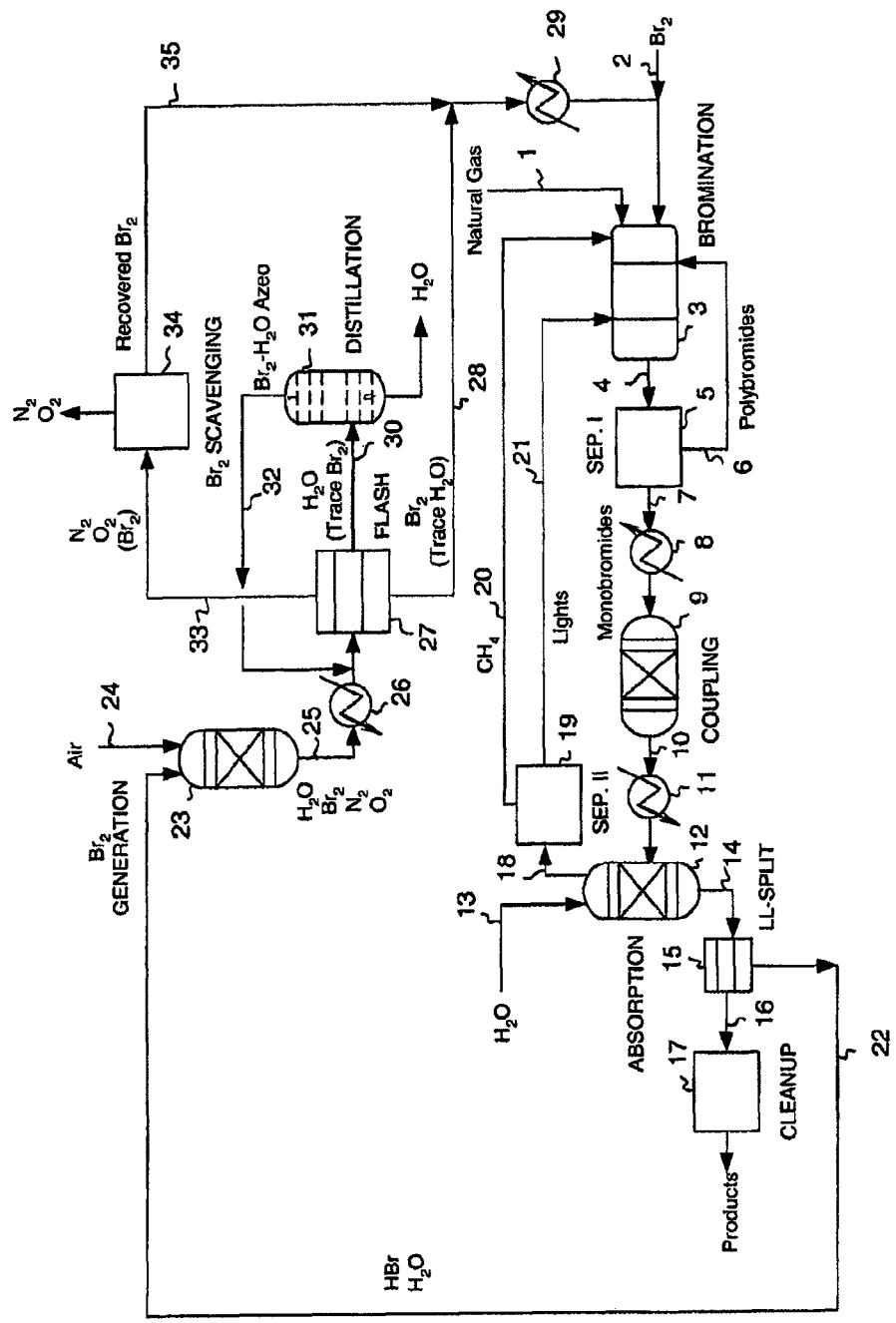
FIG. 1 is a schematic view of one embodiment of a continuous process for converting methane or natural gas into hydrocarbon chemicals according to the invention.

This invention generally relates to carbon-carbon coupling and, more particularly, to methods for converting hydrocarbon feedstocks into useful products.

The present invention provides a chemical process that enables natural gas and other hydrocarbon feedstocks to be converted into higher molecular weight hydrocarbon products, using molecular halogen to activate C—H bonds in the feedstock. According to one aspect of the invention, a continuous process for converting a hydrocarbon feedstock into one or more higher hydrocarbons comprises the steps of (a) forming alkyl halides by reacting molecular halogen with a hydrocarbon feedstock (preferably a feedstock containing methane), under process conditions sufficient to form alkyl halides and hydrogen halide, whereby substantially all of the molecular halogen is consumed; (b) forming reproportionated alkyl halides by reacting some or all of the alkyl halides with an alkane feed, whereby the fraction of monohalogenated hydrocarbons present is increased; (c) contacting the reproportionated alkyl halides with a first catalyst under process conditions sufficient to form higher hydrocarbons and additional hydrogen halide; (d) separating the higher hydrocarbons from the hydrogen halide; (e) regenerating molecular halogen by contacting the hydrogen halide with a second catalyst in the presence of a source of oxygen, under process conditions sufficient to form molecular halogen and water; (f) separating the molecular halogen from water to allow reuse of the halogen; and (g) repeating steps (a) through (f) a desired number of times. These steps can be carried out in the order presented or, alternatively, in a different order.

According to a second aspect of the invention, a continuous process for converting a hydrocarbon feedstock into one or more higher hydrocarbons comprises the steps of (a) forming alkyl halides by reacting molecular halogen with a hydrocarbon feedstock containing methane in a halogenation reactor, under process conditions sufficient to form alkyl halides and hydrogen halide, whereby substantially all of the molecular halogen is consumed; (b) separating unreacted methane from the alkyl halides and directing it back into the halogenation reactor; (c) forming reproportionated alkyl halides by reacting some or all, of the alkyl halides with an alkane feed containing at least 1% by volume of one or more C2-C5 hydrocarbons, whereby the fraction of monohalogenated hydrocarbons present is increased; (d) contacting the reproportionated alkyl halides with a first catalyst under process conditions sufficient to form higher hydrocarbons and additional hydrogen halide; (e) separating the higher hydrocarbons from the hydrogen halide; (f) regenerating molecular halogen by contacting the hydrogen halide with a second catalyst in the presence of a source of oxygen, under process conditions sufficient to form molecular halogen and water; (g) separating the molecular halogen from water to allow reuse of the halogen; and (h) repeating steps (a) through (g) a desired number of times.

In each of the aspects and embodiments of the invention, it is intended that the alkyl halides formed in step (a) can be all the same (e.g., 100% bromomethane) or, more typically, different (e.g., mixtures of bromomethane, dibromomethane, dibromoethane, etc). Similarly, it is contemplated that the "higher hydrocarbons" formed in step (c) can be all the same (e.g., 100% isooctane) or, more typically, different (e.g., mixtures of aliphatic and/or aromatic compounds). As used herein, the term "higher hydrocarbons" refers to hydrocarbons having a greater number of carbon atoms than one or more components of the hydrocarbon feedstock, as well as olefinic hydrocarbons having the same or a greater number of carbon atoms as one or more components of the hydrocarbon feedstock. For instance, if the feedstock is natural gas—typically a mixture of light hydrocarbons, predominately methane, with lesser amounts of ethane, propane, and butane, and even smaller amounts of longer chain hydrocarbons such as pentane, hexane, etc.—the "higher hydrocarbon(s)" produced according to the invention can include a $C_2$ or higher hydrocarbon, such as ethane, propane, butane, $C_{5+}$ hydrocarbons, aromatic hydrocarbons, etc., and optionally ethylene, propylene, and/or longer olefins The term "light hydrocarbons" (sometimes abbreviated "LHCs") refers to $C_1$-$C_4$ hydrocarbons, e.g., methane, ethane, propane, ethylene, propylene, butanes, and butenes, all of which are normally gases at room temperature and atmospheric pressure.

Nonlimiting examples of hydrocarbon feedstocks appropriate for use in the present invention include alkanes, e.g., methane, ethane, propane, and even larger alkanes; olefins; natural gas and other mixtures of hydrocarbons. In most cases, the feedstock will be primarily aliphatic in nature. Certain oil refinery processes yield light hydrocarbon streams (so-called "light-ends," typically a mixture of $C_1$-$C_3$ hydrocarbons), which can be used with or without added methane as the hydrocarbon feedstock in one embodiment of the invention.

Representative halogens include bromine ($Br_2$) and chlorine ($Cl_2$). It is also contemplated that fluorine and iodine can be used, though not necessarily with equivalent results. Some of the problems associated with fluorine can likely be addressed by using dilute streams of fluorine (e.g., fluorine gas carried by helium, nitrogen, or other diluent). It is expected, however, that more vigorous reaction conditions will be required for alkyl fluorides to couple and form higher hydrocarbons, due to the strength of the fluorine-carbon bond. Similarly, problems associated with iodine (such as the endothermic nature of certain iodine reactions) can likely be addressed by carrying out the halogenation and/or coupling reactions at higher temperatures and/or pressures. The use of bromine or chlorine is preferred, with bromine being most preferred.

Figure 2:
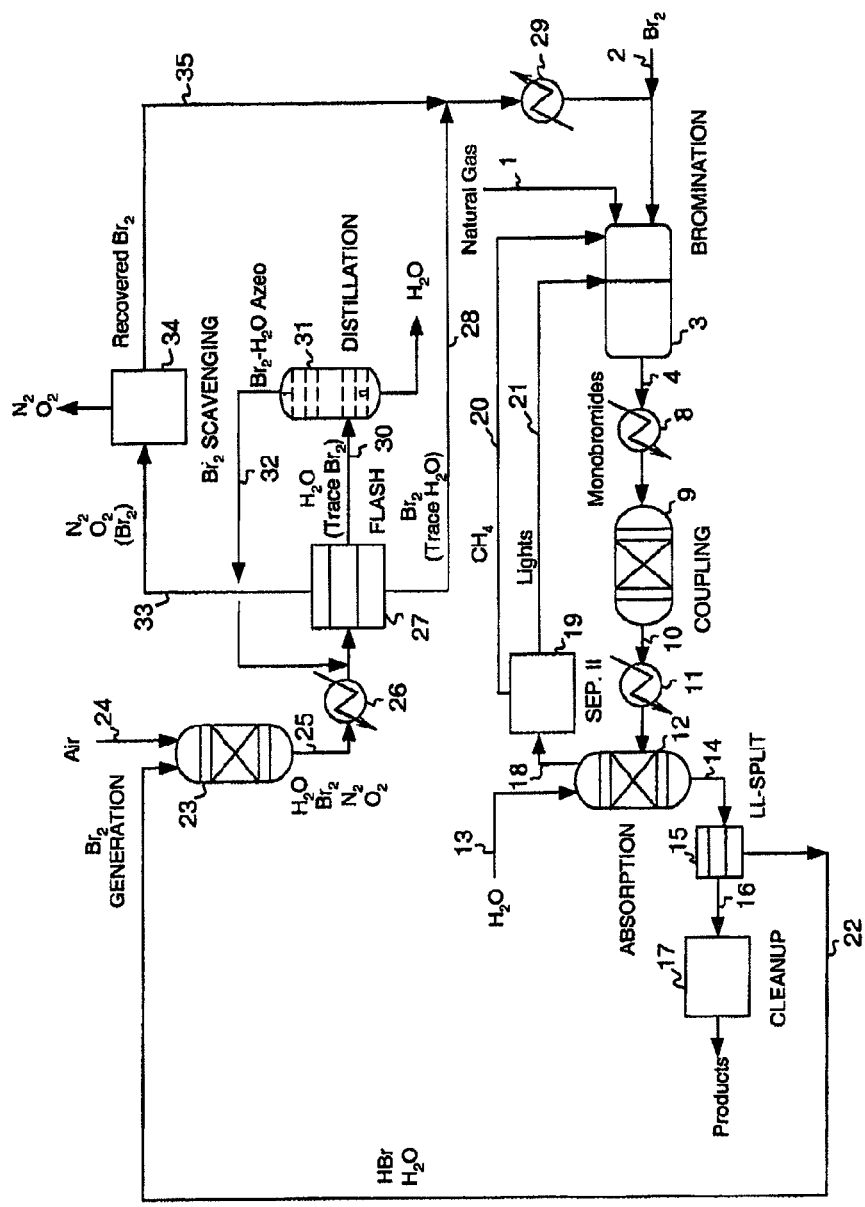
FIG. 2 is a schematic view of one embodiment of a continuous process for converting methane or natural gas into hydrocarbon fuels according to the invention.

FIGS. 1 and 2 schematically illustrate two nonlimiting embodiments of a process according to the invention, with FIG. 1 depicting a process for making hydrocarbon chemicals (e.g., benzene, toluene, xylenes, other aromatic compounds, etc.), and FIG. 2 depicting a process for making fuel-grade hydrocarbons, e.g., hydrocarbons comprising a predominant amount of $C_5$ and higher aliphatic hydrocarbons and (optionally) aromatic hydrocarbons. The primary difference in the two embodiments is that the process depicted in FIG. 2 lacks the first separation unit (SEP I) and does not return polybrominated species to the bromination reactor for "reproportionation." In the scheme shown in FIG. 2, the amount of polybromides produced is reduced significantly by introducing light gasses into the bromination reactor. The polybromides (from methane bromination) react with the light gasses to form monobromoalkanes. For convenience, the figures depict a bromine-based process. In alternate embodiments of the invention, however, chlorine or other halogens are used.

As shown in FIG. 1, natural gas (or another hydrocarbon feedstock) and molecular bromine are carried by separate lines 1, 2 into a heated bromination reactor 3 and allowed to react. Products (HBr, alkyl bromides, optionally olefins), and possibly unreacted hydrocarbons, exit the reactor and are carried by a line 4 into a first separation unit 5 (SEP I), where monobrominated hydrocarbons and HBr are separated from polybrominated hydrocarbons. The polybromides are carried by a line 6 back to the bromination reactor, where they undergo "reproportionation" with methane and/or other light hydrocarbons, which are present in the natural gas and/or introduced to the bromination reactor as described below.

Reproportionation of the polybromides formed during the bromination reaction enriches the outlet stream with monobromides and olefinic species, and reduces the amount of polybrominated hydrocarbons that enter the coupling reactor. This, in turn, reduces the amount of coke that forms during the carbon-carbon coupling reactions. For large scale production of aromatic hydrocarbons, it is possible to employ additional separation units, which can further purify the feed stream to the coupling reactor by separating and recycling the polybromides, thereby reducing the amount of coke and the overall bromine requirement.

Unreacted hydrocarbon feedstock, HBr, monobromides, and (optionally) olefins formed in the bromination reactor are carried by a line 7, through a heat exchanger 8, and enter a heated coupling reactor 9, where the monobromides (and, optionally, any olefins present) react in the presence of a coupling catalyst to form higher hydrocarbons. HBr, higher hydrocarbons, and (possibly) unreacted hydrocarbons and alkyl bromides exit the coupling reactor and are carried by a line 10, through another heat exchanger 11, and enter an HBr absorption unit 12. Water is introduced into the unit through a separate line 13. HBr is absorbed in this unit, which may be a packed column or other gas-liquid contacting device. The effluent, containing liquid hydrocarbons and aqueous HBr, is carried by a line 14 to a liquid-liquid splitter 15, which phase-separates liquid hydrocarbons from the aqueous HBr stream. The liquid hydrocarbon products are then carried by a line 16 to a product clean-up unit 17 to yield final hydrocarbon products.

After HBr is separated from the hydrocarbon products and unreacted methane (and any other light hydrocarbons that may be present) in the HBr absorption unit, the methane (and other light hydrocarbons, if any) is carried by a line 18 into a second separation unit 19 (SEP II), which employs pressure- or temperature-swing adsorption, membrane-based separation, cryogenic distillation (preferable for large scale production), or another suitable separation technology. Methane, and possibly other light hydrocarbons, are returned to the bromination reactor via one or more lines 20, 21. In the embodiment shown, methane is directed to an upstream region or "zone" of the bromination reactor, while other light hydrocarbons are directed to a mid- or downstream zone of the reactor (the latter to facilitate reproportionation of polybromides).

The aqueous HBr stream that evolves from the liquid-liquid splitter is carried by a line 22 to a bromine generation unit 23. Oxygen, air, or oxygen-enriched gas is also fed into the unit through a separate line 24. Bromine is regenerated by reacting HBr with oxygen in the presence of a suitable catalyst. The resulting stream contains water, molecular bromine, oxygen, nitrogen (if air was used as the source of oxygen), and possibly other gases. This product stream is carried by a line 25 through a heat exchanger 26 into a flash vaporization unit 27, which separates most of the molecular bromine from water, oxygen, nitrogen, and other gases (if any) that are present. Molecular bromine, either as a liquid or vapor (and containing no more than a trace of $H_2O$), is carried by a line 28 to a heat exchanger 29, and then returned to the bromination reactor.

Water from the flash vaporization unit (containing up to 3 wt % of molecular bromine) is sent by a line 30 to a distillation unit 31, which yields water as the bottoms stream and bromine or bromine-water azeotrope as a distillate. The distillate is returned through a line 32 back to the flash vaporization unit.

The gaseous products of the flash vaporization unit (e.g., oxygen, nitrogen, optionally other gases, and no more than a minor or trace amount of bromine) are carried by a line 33 to a bromine scavenging unit 34, which separates molecular bromine from the other gases. The recovered bromine is then carried by a line 35 through a heat exchanger 29 and reintroduced into the bromination reactor. The amount of bromine entering the scavenger can be further reduced by increasing the amount of bromine recovered in the flash step by employing brine solutions and direct contact cooling to allow the use of temperatures below 0° C. The other gases (e.g., nitrogen, oxygen) can be vented to the atmosphere.

Various embodiments and features of individual subprocesses and other improvements for carrying out the invention will now be described in more detail.

Bromination

Bromination of the hydrocarbon feedstock is carried out in a fixed bed, fluidized bed, or other suitable reactor, at a temperature and pressure such that the bromination products and reactants are gases, for example, 1-50 atm, 150-600° C., more preferably 400-600° C., even more preferably, 450-515° C., with a residence time of 1-60 seconds, more preferably 1-15 seconds. Higher temperatures tend to favor coke formation, while low temperatures require larger reactors. Using a fluidized bed offers the advantage of improved heat transfer.

Alkane bromination can be initiated using heat or light, with thermal means being preferred. In one embodiment, the reactor also contains a halogenation catalyst, such as a zeolite, amorphous alumino-silicate, acidic zirconia, tungstates, solid phosphoric acids, metal oxides, mixed metal oxides, metal halides, mixed metal halides (the metal in such cases being, e.g., nickel, copper, cerium, cobalt, etc.), and/or or other catalysts as described, e.g., in U.S. Pat. Nos. 3,935,289 and 4,971,664. In an alternate embodiment, the reactor contains a porous or non-porous inert material that provides sufficient surface area to retain coke formed in the reactor and prevent it from escaping. The inert material may also promote the formation of polyhalogenated hydrocarbons, such as tribromopropane. In still another embodiment, both a catalyst and an inert material are provided in the reactor. Optionally, the reactor contains different regions or zones to allow, in or more zones, complete conversion of molecular bromine to produce alkyl bromides and hydrogen bromide.

The bromination reaction can also be carried out in the presence of an isomerization catalyst, such as a metal bromide (e.g., NaBr, KBr, CuBr, $NiBr_2$, $MgBr_2$, $CaBr_2$), metal oxide (e.g., $SiO_2$, $ZrO_2$, $Al_2O_3$), or metal (Pt, Pd, Ru, Ir, Rh) to help generate the desired brominated isomer(s). Since isomerization and bromination conditions are similar, the bromination and isomerization can be carried out in the same reactor vessel. Alternatively, a separate isomerization reactor can be utilized, located downstream of the bromination reactor and upstream of the coupling reactor.

Reproportionation

In some embodiments, a key feature of the invention is the "reproportionation" of polyhalogenated hydrocarbons (polyhalides), i.e., halogenated hydrocarbons containing two or more halogen atoms per molecule. Monohalogenated alkanes (monohalides) created during the halogenation reaction are desirable as predominant reactant species for subsequent coupling reactions and formation of higher molecular weight hydrocarbons. For certain product selectivities, polyhalogenated alkanes may be desirable. Reproportionation allows a desired enrichment of monohalides to be achieved by reacting polyhalogenated alkyl halides with nonhalogenated alkanes, generally in the substantial absence of molecular halogens, to control the ratio of mono-to-polyhalogenated species. For example, dibromomethane is reacted with methane to produce methyl bromide; dibromomethane is reacted with propane to produce methyl bromide and propyl bromide and/or propylene; and so forth.

Reactive reproportionation is accomplished by allowing the hydrocarbon feedstock and/or recycled alkanes to react with polyhalogenated species from the halogenation reactor, preferably in the substantial absence of molecular halogen. As a practical matter, substantially all of the molecular halogen entering the halogenation reactor is quickly consumed, forming mono- and polyhalides; therefore reproportionation of higher bromides can be accomplished simply by introducing polybromides into a mid- or downstream region or "zone" of the halogenation reactor, optionally heated to a temperature that differs from the temperature of the rest of the reactor.

Figure 3:
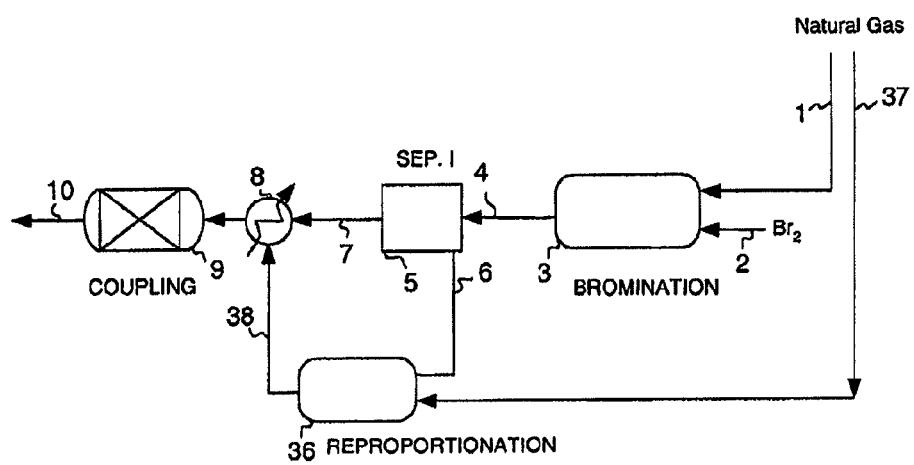
FIG. 3 is a schematic view of a subprocess for reproportionating polyhalides according to an alternate embodiment of the invention.

Alternatively, reproportionation can be carried out in a separate "reproportionation reactor," where polyhalides and unhalogenated alkanes are allowed to react, preferably in the substantial absence of molecular halogen. FIG. 3 illustrates one such embodiment where, for clarity, only significant system elements are shown. As in FIG. 1, natural gas or another hydrocarbon feedstock and molecular bromine are carried by separate lines 1, 2 to a heated bromination reactor 3 and allowed to react. Products (HBr, alkyl bromides) and possibly unreacted hydrocarbons, exit the reactor and are carried by a line 4 into a first separation unit 5 (SEP I), where monobrominated hydrocarbons and HBr are separated from polybrominated hydrocarbons. The monobromides, HBr, and possibly unreacted hydrocarbons are carried by a line 7, through a heat exchanger 8, to a coupling reactor 9, and allowed to react, as shown in FIG. 1. The polybromides are carried by a line 6 to a reproportionation reactor 36. Additional natural gas or other alkane feedstock is also introduced into the reproportionation reactor, via a line 37. Polybromides react with unbrominated alkanes in the reproportionation reactor to form monobromides, which are carried by a line 38 to the coupling reactor 9, after first passing through a heat exchanger.

In another embodiment of the invention (not shown), where the hydrocarbon feedstock comprises natural gas containing a considerable amount of C2 and higher hydrocarbons, the "fresh" natural gas feed is introduced directly into the reproportionation reactor, and recycled methane (which passes through the reproportionation reactor unconverted) is carried back into the halogenation reactor.

Reproportionation is thermally driven and/or facilitated by use of a catalyst. Nonlimiting examples of suitable catalysts include metal oxides, metal halides, and zeolites. U.S. Pat. No. 4,654,449 discloses the reproportionation of polyhalogenated alkanes with alkanes using an acidic zeolite catalyst. U.S. Pat. Nos. 2,979,541 and 3,026,361 disclose the use of carbon tetrachloride as a chlorinating agent for methane, ethane, propane and their chlorinated analogues. All three patents are incorporated by reference herein in their entirety. Using reproportionation in the context of a continuous process for the enrichment of reactive feed stocks for the production of higher hydrocarbons has never been disclosed to our knowledge.

Reproportionation of C1-C5 alkanes with dibromomethane and/or other polybromides occurs at temperatures ranging from 350 to 550° C., with the optimal temperature depending on the polybromide(s) that are present and the alkane(s) being brominated. In addition, reproportionation proceeds more quickly at elevated pressures (e.g., 2-30 bar). By achieving a high initial methane conversion in the halogenation reactor, substantial amounts of di- and tribromomethane are created; those species can then be used as bromination reagents in the reproportionation step. Using di- and tribromomethane allows for controlled bromination of C1-C5 alkanes to monobrominated C1-C5 bromoalkanes and C2-C5 olefins. Reproportionation of di- and tribromomethane facilitates high initial methane conversion during bromination, which should reduce the methane recycle flow rate and enrich the reactant gas stream with C2-C5 monobromoalkanes and olefins, which couple to liquid products over a variety of catalysts, including zeolites. This is a major new process advance.

In another embodiment of the invention, reproportionation is carried out without first separating the polyhalides in a separation unit. This is facilitated by packing the "reproportionation zone" with a catalyst, such as a zeolite, that allows the reaction to occur at a reduced temperature. For example, although propane reacts with dibromomethane to form bromomethane and bromopropane (an example of "reproportionation"), the reaction does not occur to an appreciable degree at temperatures below about 500° C. The use of a zeolite may allow reproportionation to occur at a reduced temperature, enabling species such as methane and ethane to be brominated in one zone of the reactor, and di-, tri-, and other polybromides to be reproportionated in another zone of the reactor.

Bromine Recovery During Decoking

Inevitably, coke formation will occur in the halogenation and reproportionation processes. If catalysts are used in the reactor(s) or reactor zone(s), the catalysts may be deactivated by the coke; therefore, periodic removal of the carbonaceous deposits is required. In addition, we have discovered that, within the coke that is formed, bromine may also be found, and it is highly desirable that this bromine be recovered in order to minimize loss of bromine in the overall process, which is important for both economic and environmental reasons.

Several forms of bromides are present: HBr, organic bromides such as methyl bromide and dibromomethane, and molecular bromine. The invention provides means for recovering this bromine from the decoking process. In a preferred embodiment, a given reactor is switched off-line and air or oxygen is introduced to combust the carbon deposits and produce HBr from the residual bromine residues. The effluent gas is added to the air (or oxygen) reactant stream fed to the bromine generation reactor, thereby facilitating complete bromine recovery. This process is repeated periodically.

While a given reactor is off-line, the overall process can, nevertheless, be operated without interruption by using a reserve reactor, which is arranged in parallel with its counterpart reactor. For example, twin bromination reactors and twin coupling reactors can be utilized, with process gasses being diverted away from one, but not both, bromination reactors (or coupling reactors) when a decoking operation is desired. The use of a fluidized bed may reduce coke formation and facilitate the removal of heat and catalyst regeneration.

Another embodiment of the decoking process involves non-oxidative decoking using an alkane or mixture of alkanes, which may reduce both the loss of adsorbed products and the oxygen requirement of the process. In another embodiment of the decoking process, an oxidant such as oxygen, air, or enriched air is co-fed into the bromination section to convert the coke into carbon dioxide and/or carbon monoxide during the bromination reaction, thus eliminating or reducing the off-line decoking requirement.

Alkyl Halide Separation

The presence of large concentrations of polyhalogenated species in the feed to the coupling reactor can result in an increase in coke formation. In many applications, such as the production of aromatics and light olefins, it is desirable to feed only monohalides to the coupling reactor to improve the conversion to products. In one embodiment of the invention, a specific separation step is added between the halogenation/reproportionation reactor(s) and the coupling reactor.

For example, a distillation column and associated heat exchangers ("SEP I" in FIGS. 1 and 2) can be used to separate the monobromides from the polybrominated species by utilizing the large difference in boiling points of the compounds. The polybrominated species that are recovered as the bottoms stream can be reproportionated with alkanes to form monobromide species and olefins, either in the bromination reactor or in a separate reproportionation reactor. The distillation column can be operated at any pressure of from 1 to 50 bar. The higher pressures allow higher condenser temperatures to be used, thereby reducing the refrigeration requirement.

Figure 4:
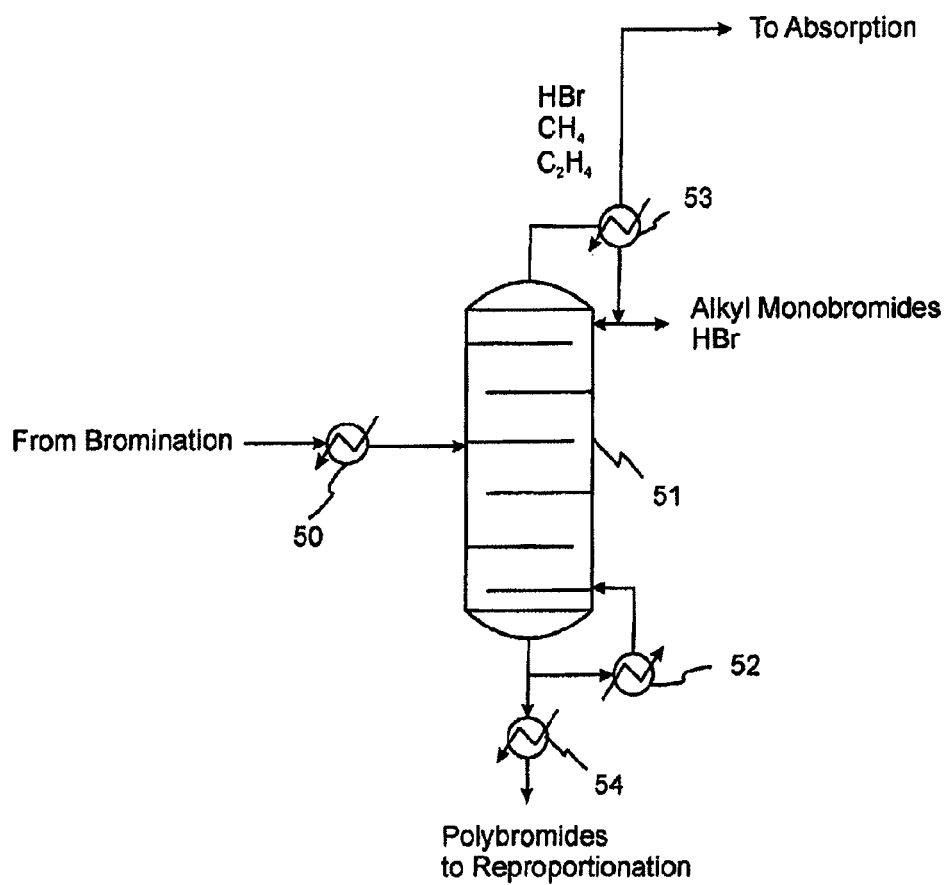
FIG. 4 is a schematic view of one embodiment of a monobromide separation column, for use in the practice of the invention.

FIG. 4 illustrates one embodiment of a separation unit for separating monobromides from polybrominated species. Alkyl bromides from the bromination reactor are cooled by passing through a heat exchanger 50, and then provided to a distillation column 51 equipped with two heat exchangers 52 and 53. At the bottom of the column, heat exchanger 52 acts as a reboiler, while at the top of the column heat exchanger 53 acts as a partial condenser. This configuration allows a liquid "bottoms" enriched in polybromides (and containing no more than a minor amount of monobromides) to be withdrawn from the distillation column. The polybromides are passed through another heat exchanger 54 to convert them back to a gas before they are returned to the bromination reactor (or sent to a separate reproportionation reactor) for reproportionation with unbrominated alkanes. At the top of the column, partial reflux of the liquid from the reflux drum is facilitated by the heat exchanger 53, yielding a vapor enriched in lighter components including methane and HBr, and a liquid stream comprised of monobromides and HBr (and containing no more than a minor amount of polybromides).

Alternate distillation configurations include a side stream column with and without a side stream rectifier or stripper. If the feed from the bromination reactor contains water, the bottoms stream from the distillation column will also contain water, and a liquid-liquid phase split on the bottoms stream can be used to separate water from the polybrominated species. Due to the presence of HBr in the water stream, it can either be sent to a HBr absorption column or to the bromine generation reactor.

Catalytic Coupling of Alkyl Halides to Higher Molecular Weight Products

The alkyl halides produced in the halogenation/reproportionation step are reacted over a catalyst to produce higher hydrocarbons and hydrogen halide. The reactant feed can also contain hydrogen halide and unhalogenated alkanes from the bromination reactor. According to the invention, any of a number of catalysts are used to facilitate the formation of higher hydrocarbon products from halogenated hydrocarbons. Nonlimiting examples include non-crystalline alumino silicates (amorphous solid acids), tungsten/zirconia super acids, sulfated zirconia, alumino phosphates such as SAPO-34 and its framework-substituted analogues (substituted with, e.g., Ni or Mn), Zeolites, such as ZSM-5 and its ion-exchanged analogs, and framework substituted ZSM-5 (substituted with Ti, Fe, Ti+Fe, B, or Ga). Preferred catalysts for producing liquid-at-room-temperature hydrocarbons include ion-exchanged ZSM-5 having a $SiO_2/Al_2O_3$ ratio below 300, preferably below 100, and most preferably 30 or below. Nonlimiting examples of preferred exchanged ions include ions of Ag, Ba, Bi, Ca, Fe, Li, Mg, Sr, K, Na, Rb, Mn, Co, Ni, Cu, Ru, Pb, Pd, Pt, and Ce. These ions can be exchanged as pure salts or as mixtures of salts. The preparation of doped zeolites and their use as carbon-carbon coupling catalysts is described in Patent Publication No. US 2005/0171393 A1, at pages 4-5, which is incorporated by reference herein in its entirety.

In one embodiment of the invention a Mn-exchanged ZSM-5 zeolite having a $SiO_2/Al_2O_3$ ratio of 30 is used as the coupling catalyst. Under certain process conditions, it can produce a tailored selectivity of liquid hydrocarbon products.

Coupling of haloalkanes preferably is carried out in a fixed bed, fluidized bed, or other suitable reactor, at a suitable temperature (e.g., 150-600° C., preferably 275-425° C.) and pressure (e.g., 0.1 to 35 atm) and a residence time ($\tau$) of from 1-45 seconds. In general, a relatively long residence time favors conversion of reactants to products, as well as product selectivity, while a short residence time means higher throughput and (possibly) improved economics. It is possible to direct product selectivity by changing the catalyst, altering the reaction temperature, and/or altering the residence time in the reactor. For example, at a moderate residence time of 10 seconds and a moderate temperature of 350° C., xylene and mesitylenes are the predominant components of the aromatic fraction (benzene+toluene+xylenes+mesitylenes; "BTXM") produced when the product of a methane bromination reaction is fed into a coupling reactor packed with a metal-ion-impregnated ZSM-5 catalyst, where the impregnation metal is Ag, Ba, Bi, Ca, Co, Cu, Fe, La, Li, Mg, Mn, Ni, Pb, Pd, or Sr, and the ZSM-5 catalyst is Zeolyst CBV 58, 2314, 3024, 5524, or 8014, (available from Zeolyst International (Valley Forge, Pa.)). At a reaction temperature of 425° C. and a residence time of 40 seconds, toluene and benzene are the predominant products of the BTXM fraction. Product selectivity can also be varied by controlling the concentration of dibromomethane produced or fed into the coupling reactor. Removal of reaction heat and continuous decoking and catalyst regeneration using a fluidized bed reactor configuration for the coupling reactor is anticipated in some facilities.

In one embodiment, the coupling reaction is carried out in a pair of coupling reactors, arranged in parallel. This allows the overall process to be run continuously, without interruption, even if one of the coupling reactors is taken off line for decoking or for some other reason. Similar redundancies can be utilized in the bromination, product separation, halogen generation, and other units used in the overall process.

Hydrocarbon Product Separation and Halogen Recovery

The coupling products include higher hydrocarbons and HBr. In the embodiments shown in FIGS. 1 and 2, products that exit the coupling reactor are first cooled in a heat exchanger and then sent to an absorption column. HBr is absorbed in water using a packed column or other contacting device. Input water and the product stream can be contacted either in a co-current or counter-current flow, with the counter-current flow preferred for its improved efficiency. HBr absorption can be carried out either substantially adiabatically or substantially isothermally. In one embodiment, the concentration of hydrobromic acid after absorption ranges from 5 to 70 wt %, with a preferred range of 20 to 50 wt %. The operating pressure is 1 to 50 bar, more preferably 1 to 30 bar. In the laboratory, a glass column or glass-lined column with ceramic or glass packing can be used. In a pilot or commercial plant, one or more durable, corrosion-resistant materials (described below) are utilized.

In one embodiment of the invention, the hydrocarbon products are recovered as a liquid from the HBr absorption column. This liquid hydrocarbon stream is phase-separated from the aqueous HBr stream using a liquid-liquid splitter and sent to the product cleanup unit. In another embodiment, the hydrocarbon products are recovered from the HBr column as a gas stream, together with the unconverted methane and other light gases. The products are then separated and recovered from the methane and light gases using any of a number of techniques. Nonlimiting examples include distillation, pressure swing adsorption, and membrane separation technologies.

In some embodiments, the product clean-up unit comprises or includes a reactor for converting halogenated hydrocarbons present in the product stream into unhalogenated hydrocarbons. For example, under certain conditions, small amounts of C1-C4 bromoalkanes, bromobenzene, and/or other brominated species are formed and pass from the coupling reactor to the liquid-liquid splitter 16 and then to the product clean-up unit 17. These brominated species can be "hydrodehalogenated" in a suitable reactor. In one embodiment, such a reactor comprises a continuous fixed bed, catalytic converter packed with a supported metal or metal oxide catalyst. Nonlimiting examples of the active component include copper, copper oxide, palladium, and platinum, with palladium being preferred. Nonlimiting examples of support materials include active carbon, alumina, silica, and zeolites, with alumina being preferred. The reactor is operated at a pressure of 0-150 psi, preferably 0-5 psi, and a temperature of 250-400° C., preferably 300-350° C., with a GHSV of 1200-60 $hr^{-1}$, preferably about 240 $hr^{-1}$. When bromobenzene (e.g.) is passed over such a reactor, it is readily converted to benzene and HBr, with some light hydrocarbons (e.g., C3-C7) produced as byproducts. Although carbon deposition (coking) can deactivate the catalyst, the catalyst can be regenerated by exposure to oxygen and then hydrogen at, e.g., 500° C. and 400° C., respectively.

After HBr is separated from the hydrocarbon products, the unconverted methane leaves with the light gases in the vapor outlet of the HBr absorption unit. In one embodiment of the invention, unconverted methane is separated from the light gases in a separation unit ("SEP II" in the FIGS.), which operates using pressure or temperature swing adsorption, membrane-based separation, cryogenic distillation (preferable for large-scale production), or some other suitable separation process. Low methane conversions in the bromination reactor may result in the coupling products being carried with the light gases, which in turn would necessitate the recovery of these species from the lights gases. Separation technologies that can be employed for this purpose include, but are not limited to, distillation, pressure or temperature swing adsorption, and membrane-based technologies.

Figure 5:
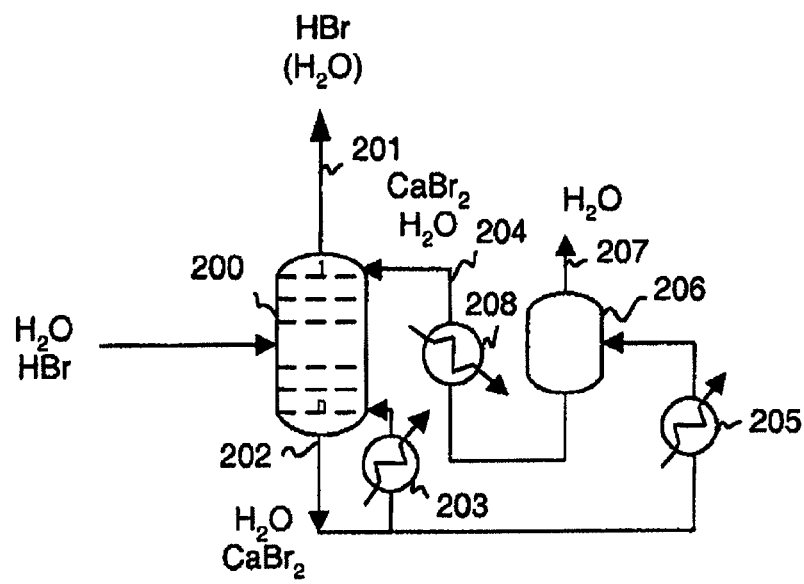
FIG. 5 is a schematic view of one embodiment of an extractive distillation system, for use in the practice of the invention.

In another aspect of the invention, a process for separating anhydrous HBr from an aqueous solution of HBr is provided. HBr forms a high-boiling azeotrope with water; therefore, separation of HBr from the aqueous solution requires either breaking the azeotrope using an extractive agent or bypassing the azeotrope using pressure swing distillation. FIG. 5 illustrates one embodiment of an extractive distillation unit for separating HBr from water. Water is extracted in a distillation column 200 and HBr is obtained as the distillate stream 201. The distillate stream may also contain small amounts of water. In one embodiment, the distillation column 200 is a tray-tower or a packed column. Conventional ceramic packing is preferred over structured packing Aqueous bromide salt, such as $CaBr_2$, is added at the top of the distillation column, resulting in the extraction of water from aqueous HBr. A condenser may not be required for the column. A reboiler 203 is used to maintain the vapor flow in the distillation column. The diluted stream of aqueous $CaBr_2$ 202 is sent to the evaporation section 206, which, optionally has a trayed or packed section. The bottoms stream from the column is heated before entering the evaporation section. Stream 207 comprising mostly water (and no more than traces of HBr) leaves the evaporation section.

In one embodiment, HBr is displaced as a gas from its aqueous solution in the presence of an electrolyte that shares a common ion ($Br^-$ or $H^+$) or an ion (e.g. $Ca^{2+}$ or $SO_4^{2-}$) that has a higher hydration energy than HBr. The presence of the electrolyte pushes the equilibrium $HBr_{aq} \leftrightarrow HBr_{gas}$ towards gas evolution, which is further facilitated by heating the solution.

Aqueous solutions of metal bromides such as $CaBr_2$, $MgBr_2$ also KBr, NaBr, LiBr, RbBr, CsBr, $SrBr_2$, $BaBr_2$, $MnBr_2$, $FeBr_2$, $FeBr_3$, $CoBr_2$, $NiBr_2$, $CuBr_2$, $ZnBr_2$, $CdBr_2$, $AlBr_3$, $LaBr_3$, $YBr_3$, and $BiBr_3$ can be used as extractive agents, with aqueous solutions of $CaBr_2$, $MgBr_2$, KBr, NaBr, LiBr or mixtures thereof being preferred. The bottoms stream of the distillation column contains a diluted solution of the extracting agent. This stream is sent to another distillation column or a vaporizer where water is evaporated and the extracting agent is concentrated before sending it back to the extractive distillation column. Sulfuric acid can be used as an extracting agent if its reaction with HBr to form bromine and sulfur dioxide can be minimized. Experiments carried out to demonstrate the separation of anhydrous HBr from an aqueous solution of HBr are described in Examples 2 and 3.

In another aspect of the invention, various approaches to product clean-up (separation and/or purification) are provided. A number of bromide species may be present in the unpurified product stream: HBr, organic bromides such as methyl bromide and dibromomethane, and bromo-aromatics. In one embodiment of the invention, hydrocarbon products are separated from brominated species by passing the product stream over copper metal, NiO, CaO, ZnO, MgO, BaO, or combinations thereof. Preferably, the products are run over one or more of the above-listed materials at a temperature of from 25-600° C., more preferably, 400-500° C. This process is tolerant of $CO_2$ that may be present.

In another embodiment, particularly for large-scale production of hydrocarbons, unconverted methane is separated from other light hydrocarbons as well as heavier products (e.g., benzene, toluene, etc.) using distillation. For example, in FIGS. 1 and 2, methane and other light hydrocarbons exit the absorption column through a gas outlet and are directed to a separation unit (SEP. II). Any unconverted methyl bromide will be removed with the light gases and can be recycled back to the bromination/reproportionation reactor. Heavier hydrocarbons are removed as a liquid distillate.

Molecular Halogen Generation

In one embodiment of the invention, catalytic halogen generation is carried out by reacting hydrohalic acid and molecular oxygen over a suitable catalyst. The general reaction can be represented by equation (1):

$$2HX + \tfrac{1}{2}O_2 \xrightarrow{\text{catalyst}} X_2 + H_2O \tag{1}$$

The process occurs at a range of temperatures and mole ratios of hydrohalic acid (HX) and molecular oxygen ($O_2$), i.e., 4:1 to 0.001:1 $HX/O_2$, preferably 4:1 (to fit the reaction stoichiometry), more preferably 3.5:1 (to prevent eventual HBr breatkthrough).

Halogen can be generated using pure oxygen, air, or oxygen-enriched gas, and the reaction can be run with a variety of inert nonreacting gases such as nitrogen, carbon dioxide, argon, helium, and water steam being present. Any proportion of these gases can be combined as pure gases or selected mixtures thereof, to accommodate process requirements.

A number of materials have been identified as halogen generation catalysts. It is possible to use one type of catalyst or a combination of any number, configuration, or proportion of catalysts. Oxides, halides, and/or oxy-halides of one or more metals, such as Cu, Ag, Au, Fe, Co, Ni, Mn, Ce, V, Nb, Mo, Pd, Ta, or W are representative, more preferably Mg, Ca, Sr, Ba, V, Cr, Mn, Fe, Co, Ni, Cu, Zn, or Ce. The most preferable catalysts are oxides, halides, and/or oxy-halides of Cu.

Although not bound by theory, the following equations are considered representative of the chemistry believed to take place when such materials are used to catalyze halogen formation:

$$CaO + 2HBr \rightarrow CaBr_2 + H_2O \tag{2}$$

$$CaBr_2 + \tfrac{1}{2}O_2 \rightarrow CaO + Br_2 \tag{3}$$

for metal oxides in which the metal does not change oxidation states, and $$Co_3O_4 + 8HBr \rightarrow 3CoBr_2 + 4H_2O + Br_2 \tag{4}$$

$$3CoBr_2 + 2O_2 \rightarrow Co_3O_4 + 3Br_2 \tag{5}$$

for metal oxides in which the metal does change oxidation states. The net reaction for (2)+(3) and (4)+(5) is (7):

$$2HX \xrightarrow{\text{catalyst}} X_2 + H_2O \tag{7}$$

which is equivalent to (1).

In one embodiment of the invention, chlorine is used as the halogenating agent, and ceria ($CeO_2$) is used to catalyze the generation of chlorine from hydrochloric acid. The following equations are considered representative:

$$CeO_2 + 4HCl \rightarrow CeCl_2 + H_2O + Cl_2 \quad (8)$$

$$CeCl_2 + O_2 \rightarrow CeO_2 + Cl_2 \quad (9)$$

for an overall reaction: $2HCl + \frac{1}{2}O_2 \rightarrow H_2O + Cl_2$ (10)

which is also equivalent to (1).

This use of ceria is quite novel, as it allows essentially complete consumption of HCl. In contrast, previous reactions of metal oxides, HCl, and oxygen have typically yielded $HCl/Cl_2$ mixtures. Thus, ceria can advantageously be employed as a halogen regeneration catalyst, particularly where chlorine is used for alkane halogenation, with chlorine's attendant lower cost and familiarity to industry.

In one embodiment of the invention, the halogen generation catalyst(s) are supported on porous or nonporous alumina, silica, zirconia, titania or mixtures thereof, or another suitable support. A range of temperatures can be employed to maximize process efficiency, e.g., 200-600° C., more preferably 350-450° C.

Recovery and Recycle of Molecular Halogen

Halogen generation produces both water and molecular halogen. Water can be separated from halogen and removed before the halogen is reacted with the hydrocarbon feedstock. Where the halogen is bromine, a bromine-water, liquid-liquid phase split is achieved upon condensation of a mixture of these species. For example, in one embodiment of the invention, a liquid-liquid flash unit is used to separate most of the bromine from water, simply and inexpensively. The bromine phase typically contains a very small amount of water, and can be sent directly to the bromination reactor. The water phase, however, contains 1-3 wt % bromine. However, if air is used in the bromine generation step, nitrogen and unconverted oxygen are present with the bromine and water stream that enters the flash.

The gas leaving the flash unit primarily consists of nitrogen and unconverted oxygen, but carries with it some bromine and water. The amount of bromine leaving with the vapor phase depends on the temperature and pressure of the flash. The flash can be operated at temperatures ranging from 0 to 50° C.; however, a lower temperature (ca 2 to 10° C.) is preferred to reduce bromine leaving in the vapor stream. The vapor stream is sent to the bromine scavenging section for bromine recovery. In one embodiment, the operating pressure is 1 to 50 bar, more preferably 1 to 30 bar. Since water freezes at 0° C., it is not possible to substantially reduce the temperature of the flash 19. However, the vapor stream from the flash can be contacted with a chilled brine solution, at temperatures from −30° C. to 10° C. Chilled brine temperatures lower than that of the flash can substantially reduce the bromine scavenging requirement of the scavenging unit. Vaporizing the bromine by heating the brine can then occur, with further heating employed to facilitate concentration of the brine for re-use. This approach to bromine recovery can be carried out either continuously or in batch mode.

Bromine contained in the water-rich phase leaving the liquid-liquid flash can be effectively recovered by distillation. Other means, such as using an inert gas to strip the bromine from the water phase (described by Waycuilis) and adsorption-based methods, are not very effective, and potentially can result in a significant loss of bromine. The presently described distillation subprocess produces bromine or bromine-water azeotrope as a distillate, which is recycled back to the flash unit. Water is contained in the bottoms stream. Bromine can react reversibly with water to form small amounts of HBr and HOBr. In the distillation scheme, therefore, ppm levels of HBr (and/or HOBr) can be present in the bottoms stream. A side-stream rectifier or stripper can be utilized to reduce the bromine content of the bottoms stream to produce a pure water stream. Other alternatives that can reduce the bromine content of the water to below 10 ppm range include, but are not limited to, the addition of acids such as sulfuric acid, hydrochloric acid, and phosphoric acid, in very small quantities to reduce the pH of the water stream. Lowering the pH drives the HBr and HOBr stream back to bromine and water, thereby substantially reducing the loss of bromine in the water stream. HBr present in the water stream can also be recovered using ion-exchange resins or electrochemical means.

Recovery of All Halogen for Reuse

For both economic and environmental reasons, it is preferred to minimize, if not completely eliminate, loss of halogen utilized in the overall process. Molecular bromine has the potential to leave with vented nitrogen and unconverted oxygen if it is not captured after $Br_2$ generation. Bromine scavenging can be carried out in a bed containing solid CuBr or $MnBr_2$, either loaded on a support or used in powder form, to capture $Br_2$ from a gas stream that may also contain $H_2O$, $CO_2$, $O_2$, methane &/or $N_2$. In one embodiment of the invention, bromine scavenging is performed within a range of temperatures, i.e., from −10° C. to 200° C. When bromine scavenging is complete, molecular bromine can be released from the bed by raising the temperature of the bed to 220° C. or higher, preferably above 275° C. It is important that there be little if any $O_2$ in the bed during bromine release, as $O_2$ will oxidize the metal and, over time, reduce the bromine-scavenging capacity of the bed.

Construction of Critical Process Elements with Unique Corrosion-Resistant Materials Corrosion induced by any halogen-containing process, whether in the condensed phase or the vapor phase, presents a significant challenge in the selection of durable materials for the construction of reactors, piping, and ancillary equipment. Ceramics, such as alumina, zirconia, and silicon carbides, offer exceptional corrosion resistance to most conditions encountered in the process described herein. However, ceramics suffer from a number of disadvantages, including lack of structural strength under tensile strain, difficulty in completely containing gas phase reactions (due to diffusion or mass transport along jointing surfaces), and possibly undesirable thermal transport characteristics inherent to most ceramic materials. Constructing durable, gas-tight, and corrosion resistant process control equipment (i.e. shell and tube type heat-exchangers, valves, pumps, etc.), for operation at elevated temperatures and pressures, and over extended periods of time, will likely require the use of formable metals such as Au, Co, Cr, Fe, Nb, Ni, Pt, Ta, Ti, and/or Zr, or alloys of these base metals containing elements such as Al, B, C, Co, Cr, Cu, Fe, H, Ha, La, Mn, Mo, N, Nb, Ni, O, P, Pd, S, Si, Sn, Ta, Ti, V, W, Y, and/or Zr.

According to one embodiment of the invention, the process and subprocesses described herein are carried out in reactors, piping, and ancillary equipment that are both strong enough and sufficiently corrosion-resistant to allow long-term continued operation. Selection of appropriate materials of construction depends strongly on the temperature and environment of exposure for each process control component.

Suitable materials for components exposed to cyclic conditions (e.g. oxidizing and reducing), as compared to single conditions (oxidizing or reducing), will differ greatly. Non-limiting examples of materials identified as suitable for exposure to cyclic conditions, operating in the temperature range of from 150-550° C., include Au and alloys of Ti and Ni, with the most suitable being Al/V alloyed Ti (more specifically Ti Grd-5) and Ni—Cr—Mo alloys with high Cr, low Fe, and low C content (more specifically ALLCOR®, Alloy 59, C-22, 625, and HX). Nonlimiting examples of materials identified as suitable for exposure to either acid halide to air, or molecular halogen to air cyclic conditions, in the temperature range 150-550° C., either acid halide to air, or molecular halogen to air include alloys of Fe and Ni, with the most suitable being alloys of the Ni—Cr—Mo, and Ni—Mo families. Nonlimiting examples of materials identified as suitable for single environment conditions, in the temperature range 100° C.-550° C., include Ta, Au, and alloys of Fe, Co, and Ni. For lower temperature conditions (<280° C.), suitable polymer linings can be utilized such as PTFE, FEP, and more suitably PVDF. All materials may be used independently or in conjunction with a support material such as coating, cladding, or chemical/physical deposition on a suitable low-cost material such as low-alloy steels.

Figure 6:
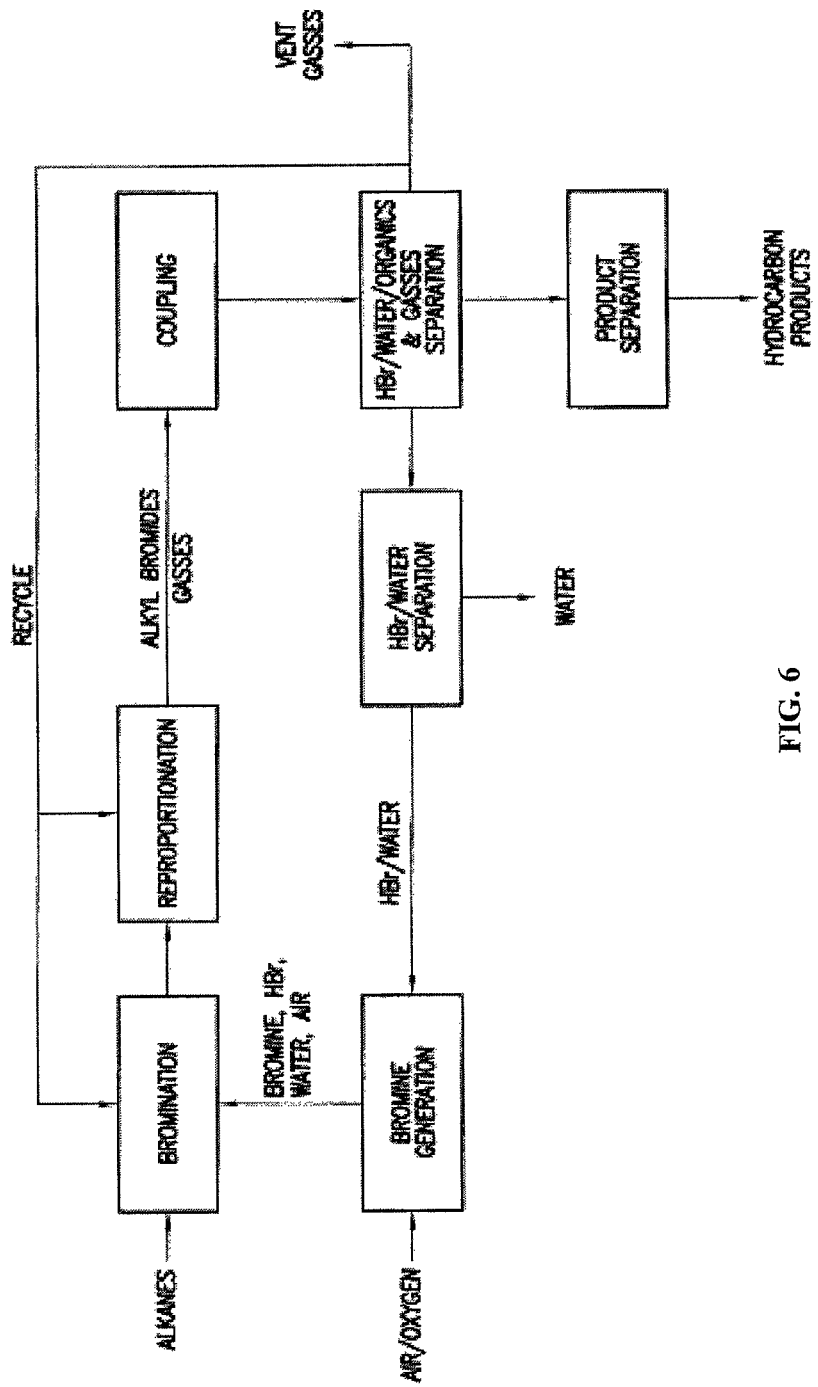
FIG. 6 is a simplified block diagram of one embodiment of a continuous process for converting alkanes into hydrocarbon products according to the invention, wherein water is separated from hydrocarbon products.

FIG. 6 schematically illustrates an alternate mode of operation for a continuous process for converting methane, natural gas, or other alkane feedstocks into higher hydrocarbons. Alkanes are brominated in the bromination section in the presence of water formed during bromine generation, including recycled water. The bromination products pass either through a reproportionation reactor or through the reproportionation section of the bromination reactor, where the light gases are reproportionated to form olefins and alkyl bromides by using the polybromides as brominating agents. The reproportionation products, which include olefins, alkyl monobromides, some polybromides, and HBr, along with any unreacted alkanes, are then sent to the coupling reactor. The coupling products are sent to a vapor-liquid-liquid flash. Higher hydrocarbon products are removed as an organic phase from the vapor-liquid-liquid flash, while aqueous HBr is removed as the heavier phase. The gas stream from the flash is sent to a separation system to recover methane and light gases, which are recycled back to the bromination and reproportionation sections, respectively.

Nitrogen must be removed from the gas recycle stream if air is used as an oxidant in bromine generation. The aqueous HBr stream coming out of the vapor-liquid-liquid flash is sent to the HBr/water separation system, where water is recovered. The separation can be carried out in a distillation column, where pure water is taken out as a distillate and the bottoms stream is an aqueous solution of HBr (having a higher concentration of HBr than the feed to the distillation column). The aqueous HBr stream is sent back to the bromine generation section, where bromine is generated from aqueous HBr in the presence of air or oxygen.

Alternatively, extractive distillation is used to separate HBr from water. The separated HBr is sent to the bromine generation reactor and bromine is generated from aqueous HBr in the presence of air or oxygen. Complete conversion of HBr is not necessary in the bromine generation reactor. Periodic decoking can be carried out for the bromination, reproportionation, and/or coupling reactors, with the bromine-containing decoking product stream being routed to the bromine generation reactor.

Figure 7:
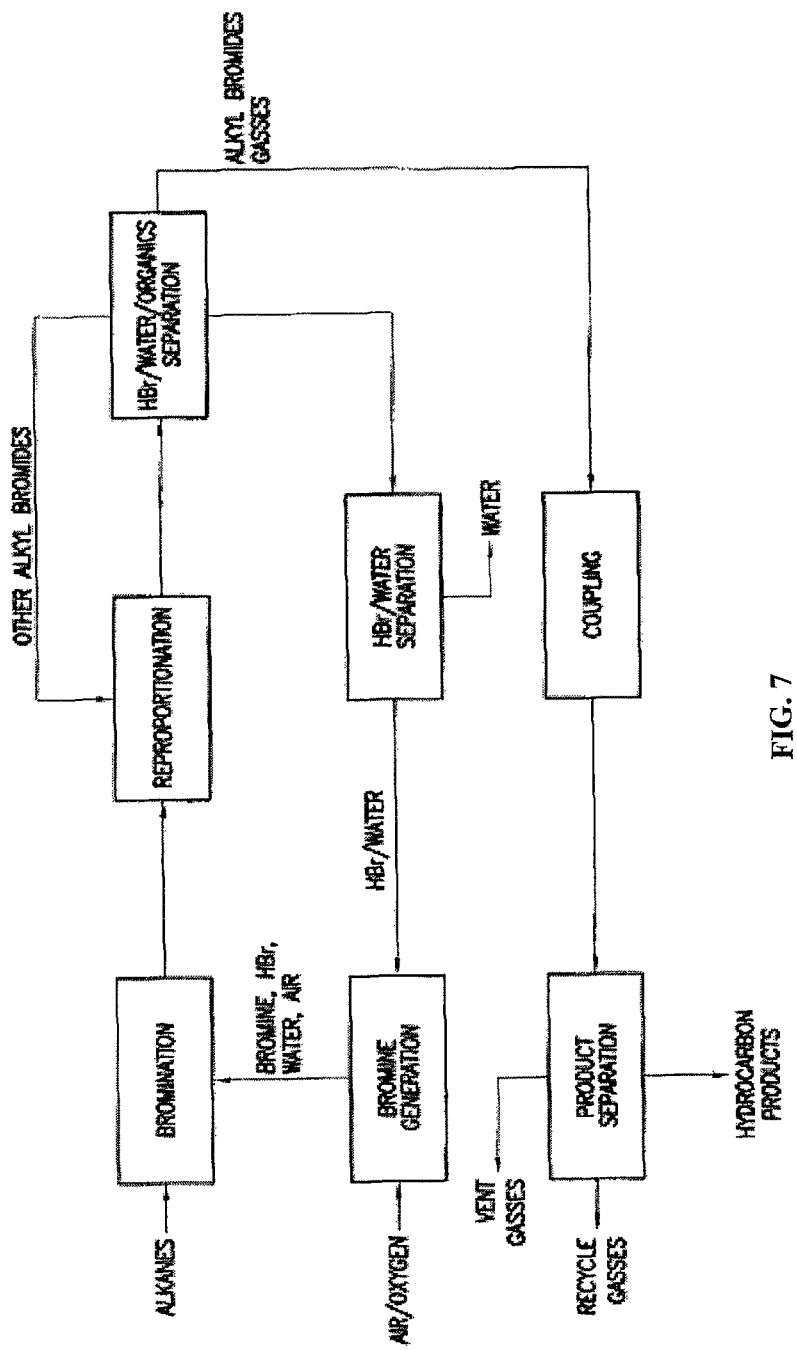
FIG. 7 is a simplified block diagram of one embodiment of a continuous process for converting alkanes into hydrocarbon products according to the invention, wherein water is separated after the alkane bromination step.

Another continuous process alternative is shown in FIG. 7. Alkanes are brominated in the bromination section in the presence of water formed during bromine generation, including recycled water. The bromination products (which include monobromides and polybromides) pass through either a reproportionation reactor or the reproportionation section of the bromination reactor, where the light gases are reproportionated to form alkyl bromides, using the polybromides as brominating agents. The reproportionation products—alkyl monobromides, olefins, a small amount of polybromides, and HBr—and any unreacted alkanes are then sent to a separation unit where aqueous HBr is separated from the alkyl bromides. Monobromides in the alkyl bromide stream are separated from the polybromides. The polybromides are recycled to the reproportionation section where polybromides react with the recycle gases to form olefins and monobromides.

The aqueous HBr separation from the alkyl bromides can be carried out in a distillation column coupled with a liquid-liquid flash. The alkyl bromide stream can contain HBr. The monobromides are fed into the coupling section, and the products are sent to a water absorption column where HBr produced in the coupling reactor is removed from the products and unconverted gas. The liquid outlet of the absorption column is fed to a vapor-liquid-liquid flash separation unit, where higher hydrocarbon products are removed as an organic phase and aqueous HBr is removed as the heavier phase. The gas outlet from the absorption column is sent to a separation system to separate methane from the light gases. The recovered methane is recycled back to the bromination section, while the light gases are recycled to the reproportionation section.

Nitrogen must be separated before the gases are recycled if air is used as an oxidant in bromine generation. The aqueous HBr stream from the vapor-liquid-liquid flash is combined with the aqueous HBr stream from the alkyl bromide separation section and sent to the HBr/Water separation system. The separation can be carried out in a distillation column, where pure water is taken out as a distillate and the bottoms stream is an aqueous solution of HBr having a higher concentration of HBr compared with the feed to the distillation column. The aqueous HBr stream is sent back to the bromine generation section, where bromine is generated from aqueous HBr in the presence of air, oxygen or enriched air.

Alternatively, extractive distillation is used to separate HBr from water. The separated HBr is sent to the bromine generation reactor, where bromine is generated from aqueous HBr in the presence of air, oxygen, or enriched air. Complete conversion of HBr to bromine is not required during bromine generation. Periodic decoking of the bromination, reproportionation and coupling reactors can be carried out, with the bromine-containing decoking product stream being routed to the bromine generation reactor.

To facilitate a better understanding of the present invention, the following examples of certain aspects of some embodiments are given. In no way should the following examples be read to limit, or define, the scope of the invention.

EXAMPLE 1

Reproportionation of Dibromomethane with Propane

Methane (11 sccm, 1 atm) was combined with nitrogen (15 sccm, 1 atm) at room temperature via a mixing tee and passed through a room temperature bubbler full of bromine. The $CH_4/N_2/Br_2$ mixture was plumbed into a preheated glass tube at 500° C., and bromination of the methane took place with a residence time ("$t_{res}$") of 60 seconds, producing primarily bromomethane, dibromomethane, and HBr. The stream of nitrogen, HBr, and partially brominated hydrocarbon was combined with propane (0.75 sccm, 1 atm) in a mixing tee and passed into a second glass reactor tube at 525° C. with a residence time ("$t_{res}$") of 60 s. In the second reactor tube, polybrominated hydrocarbons (i.e. $CH_2Br_2$, $CHBr_3$) react with the propane to produce bromopropanes. The reproportionation is idealized by the following reaction:

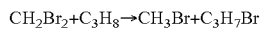
$CH_2Br_2 + C_3H_8 \rightarrow CH_3Br + C_3H_7Br$

As products left the second reactor, they were collected by a series of traps containing 4 M NaOH (which neutralized the HBr) and hexadecane (containing octadecane as an internal standard) to dissolve as much of the hydrocarbon products as possible. Volatile components like methane and propane were collected in a gas bag after the HBr/hydrocarbon traps. All products were quantified by gas chromatography. The results ("Ex. 1") are summarized in Table 1. For comparison, the reactions were also run with two reactors, but without reproportionation with propane ("Control A"), and with only the first reactor and without propane ("Control B").

TABLE 1

Reproportionation of Dibromomethane

| | Ex. 1 (bromination/reproportionation) | Control A (bromination) | Control B (bromination) |
|---|---|---|---|
| Bromination $t_{res}$ | 60 | 60 | 60 |
| Reproportionation $t_{res}$ | 60 | 60 | 0 |
| $CH_4$ conversion | 40% | 47% | 45% |
| $CH_3Br/(CH_3Br + CH_2Br_2)$ | 93% | 84% | 74% |
| $C_3H_8$ conversion | 85% | N/A | N/A |
| Carbon balance | 96% | 97% | 96% |

EXAMPLE 2

Separation of Anhydrous HBr 20 ml stock HBr aqueous solution were added to 20 g $CaBr_2H_2O$ followed by heating to 70° C. A significant evolution of HBr gas was observed (determined by $AgNO_3$ precipitation and the $NH_3$ fuming test). The released HBr was not quantified as the reaction was carried out in an open vessel.

EXAMPLE 3

Separation of Anhydrous HBr

Dehydration with $H_2SO_4$ was attempted by adding a conc. solution of $H_2SO_4$ to HBr. Qualitative tests were conducted in which different concentration of $H_2SO_4$ were added to HBr for determination of the threshold concentration where oxidation of HBr no longer occurs:

$2HBr + H_2SO_4 \rightarrow Br_2 + SO_2 + 2H_2O$

It was determined that the $H_2SO_4$ concentration below which no oxidation is apparent is about 70 wt. %. 30 ml 70% $H_2SO_4$ was added to 30 ml stock HBr azeotrope (48 wt. %) and the mixture was heated to boiling. The HBr content was determined quantitatively by $AgNO_3$ precipitation and gravimetric determination of AgBr from a solution aliquot at the moment of mixing, after 15 min and after 30 min. boiling.

EXAMPLE 4

Metathesis of Brominated Methane Over Selected Catalysts

A series of experiments were conducted in which methane was brominated in a manner substantially the same as or similar to that described in Example 1 (10 sccm methane bubbled through room temperature bromine, followed by passage of the mixture through a reactor tube heated to 500° C.), and the bromination products were then passed over various metal-ion exchanged or impregnated zeolite catalysts, at atmospheric pressure (total pressure), at a temperature of from 350 to 450° C., with a residence time of 40 seconds. Table 2 summarizes the distribution of metathesis products. Catalysts are denoted by metal ion (e.g., Ba, Co, Mn, etc.) and by type of Zeolyst Int'l. zeolite (e.g., 5524, 58, 8014, etc.). The mass (mg) of each product, as well as the total mass of products is given for each run. The abbreviations, B, PhBr, T, X, and M refer to benzene, phenyl bromide, toluene, xylene, and mesitylene, respectively.

TABLE 2

Metathesis of Brominated Methane Over Selected Catalysts

| T (C.) | Catalyst | B | PhBr | T | X | M | Total (mg) |
|---|---|---|---|---|---|---|---|
| 350 | Ba 5524 | 0.25 | 0 | 0.96 | 2.58 | 3.14 | 6.93 |
| 350 | Ba 58 | 0.31 | 0 | 1.48 | 3.2 | 3.11 | 8.11 |
| 350 | Ba 8014 | 0.3 | 0 | 1.3 | 2.87 | 3.15 | 7.6 |
| 350 | Ca 58 | 0.2 | 0 | 0.81 | 2.44 | 3.09 | 6.53 |
| 350 | Co 2314 | 1.22 | 0.02 | 3.05 | 2.18 | 0.56 | 7.04 |
| 350 | Co 3024 | 0.36 | 0 | 2.06 | 4.21 | 3.47 | 10.1 |
| 350 | Co 58 | 0.2 | 0 | 1.05 | 2.91 | 3.34 | 7.5 |
| 350 | Mg 3024 | 0.31 | 0 | 1.53 | 3.59 | 3.89 | 9.32 |
| 350 | Mg 58 | 0.28 | 0 | 1.41 | 3.3 | 3.43 | 8.42 |
| 350 | Mn 2314 | 1.07 | 0.03 | 2.86 | 2.26 | 0.65 | 6.86 |
| 350 | Mn 3024 | 0.53 | 0 | 2.92 | 4.8 | 3.02 | 11.27 |
| 350 | Mn 58 | 0.17 | 0 | 0.88 | 2.7 | 3.62 | 7.37 |
| 350 | Ni 2314 | 1.12 | 0.05 | 2.94 | 2.44 | 0.74 | 7.29 |
| 350 | Ni 3024 | 0.61 | 0 | 2.82 | 3.85 | 2.13 | 9.41 |
| 375 | Ba 5524 | 0.32 | 0 | 1.32 | 2.82 | 2.57 | 7.04 |
| 375 | Ba 58 | 0.4 | 0 | 1.84 | 2.93 | 2.4 | 7.57 |
| 375 | Ba 8014 | 0.32 | 0 | 1.23 | 2.84 | 2.95 | 7.34 |
| 375 | Ca 58 | 0.2 | 0 | 0.96 | 2.55 | 2.93 | 6.64 |
| 375 | Co 3024 | 0.47 | 0 | 2.3 | 3.52 | 2.18 | 8.48 |
| 375 | Co 58 | 0.3 | 0 | 1.54 | 2.83 | 2.42 | 7.1 |
| 375 | Mg 3024 | 0.37 | 0 | 1.81 | 3.26 | 2.78 | 8.22 |
| 375 | Mg 58 | 0.34 | 0 | 1.67 | 3.04 | 2.74 | 7.8 |
| 375 | Mn 3024 | 0.62 | 0 | 2.91 | 3.9 | 2.17 | 9.59 |
| 375 | Mn 58 | 0.22 | 0 | 1.18 | 2.71 | 2.83 | 6.94 |
| 375 | Pd 2314 | 1.54 | 0 | 3.1 | 1.83 | 0.37 | 6.85 |
| 400 | Ba 5524 | 0.46 | 0 | 2.37 | 4.16 | 2.95 | 9.94 |
| 400 | Ba 58 | 0.7 | 0 | 3.15 | 3.91 | 2.7 | 10.47 |
| 400 | Ba 8014 | 0.38 | 0 | 1.57 | 3.81 | 3.77 | 9.53 |
| 400 | Ca 58 | 0.41 | 0 | 1.89 | 3.43 | 2.81 | 8.54 |
| 400 | Co 3024 | 0.78 | 0 | 3.42 | 4.14 | 2.26 | 10.6 |
| 400 | Co 58 | 0.62 | 0 | 2.71 | 3.36 | 2.31 | 8.99 |
| 400 | Mg 3024 | 0.76 | 0 | 3.26 | 4.11 | 2.64 | 10.76 |
| 400 | Mg 58 | 0.71 | 0 | 3.04 | 3.74 | 2.59 | 10.08 |
| 400 | Mn 3024 | 0.98 | 0 | 4.1 | 4.38 | 2.06 | 11.52 |
| 400 | Mn 58 | 0.48 | 0 | 2.26 | 3.44 | 2.64 | 8.82 |
| 400 | Ni 3024 | 0.81 | 0 | 3.15 | 3.35 | 1.72 | 9.04 |
| 400 | Pb 2314 | 1.2 | 0.03 | 3.25 | 3.27 | 1.2 | 8.94 |
| 400 | Pb 3024 | 1.07 | 0.04 | 2.77 | 3.63 | 1.66 | 9.17 |
| 400 | Pd 2314 | 2.44 | 0 | 3.16 | 1.22 | 0.18 | 7.01 |
| 400 | Sr 2314 | 2.13 | 0.01 | 4.05 | 2.29 | 0.46 | 8.94 |
| 400 | Sr 3024 | 1.93 | 0.05 | 4.03 | 2.67 | 0.65 | 9.32 |
| 425 | Ag 3024 | 2.79 | 0.02 | 4.16 | 1.78 | 0.29 | 9.04 |
| 425 | Ag 8014 | 3.09 | 0.02 | 3.52 | 1.09 | 0.16 | 7.88 |
| 425 | Ba 5524 | 0.54 | 0 | 2.67 | 3.67 | 2.33 | 9.22 |
| 425 | Ba 58 | 0.79 | 0 | 3 | 2.94 | 1.75 | 8.48 |
| 425 | Bi 2314 | 3.13 | 0.03 | 4.47 | 1.61 | 0.23 | 9.48 |
| 425 | Co 2314 | 3.39 | 0.03 | 4.34 | 1.59 | 0.25 | 9.6 |
| 425 | Co 3024 | 1.07 | 0 | 3.42 | 2.79 | 1.09 | 8.38 |
| 425 | Cu 2314 | 2.89 | 0.02 | 4.74 | 2.13 | 0.37 | 10.15 |
| 425 | Li 5524 | 1.51 | 0.04 | 3.31 | 3.27 | 1.12 | 9.24 |
| 425 | Mg 3024 | 0.99 | 0 | 3.28 | 2.85 | 1.37 | 8.48 |
| 425 | Mg 58 | 0.81 | 0 | 2.62 | 2.16 | 1.11 | 6.7 |
| 425 | Mn 3024 | 1.22 | 0 | 3.9 | 3.01 | 1.14 | 9.27 |
| 425 | Mo 2314 | 3.06 | 0.04 | 4.02 | 1.46 | 0.24 | 8.82 |
| 425 | Ni 3024 | 0.97 | 0 | 3.38 | 2.85 | 1.32 | 8.51 |
| 425 | Sr 3024 | 2.53 | 0.02 | 4.36 | 2.22 | 0.43 | 9.56 |
| 450 | Ag 3024 | 3.84 | 0.02 | 4.27 | 1.36 | 0.18 | 9.67 |

TABLE 2-continued

Metathesis of Brominated Methane Over Selected Catalysts

| T (C.) | Catalyst | B | PhBr | T | X | M | Total (mg) |
|---|---|---|---|---|---|---|---|
| 450 | Bi 2314 | 3.9 | 0.01 | 3.59 | 0.67 | 0.06 | 8.23 |
| 450 | Ca 2314 | 3.64 | 0.02 | 4.1 | 1 | 0.16 | 8.92 |
| 450 | Co 2314 | 4.12 | 0.01 | 3.77 | 0.77 | 0.08 | 8.75 |
| 450 | Cu 2314 | 3.65 | 0 | 4.3 | 1.1 | 0.14 | 9.19 |
| 450 | Fe 2314 | 4.42 | 0.02 | 3.43 | 0.74 | 0.09 | 8.69 |
| 450 | Fe 3024 | 3.61 | 0.01 | 2.96 | 0.63 | 0.08 | 7.28 |
| 450 | Fe 5524 | 3.99 | 0.03 | 3.63 | 0.85 | 0.11 | 8.6 |
| 450 | La 2314 | 3.48 | 0.01 | 3.81 | 0.87 | 0.12 | 8.29 |
| 450 | Li 8014 | 1.74 | 0 | 2.61 | 2.67 | 0.84 | 7.89 |
| 450 | Mg 2314 | 4.2 | 0.02 | 3.84 | 0.76 | 0.1 | 8.92 |
| 450 | Mn 2314 | 3.78 | 0.02 | 3.9 | 0.88 | 0.12 | 8.7 |
| 450 | Mo 2314 | 3.88 | 0.01 | 3.26 | 0.58 | 0.06 | 7.79 |
| 450 | Ni 2314 | 4.39 | 0.01 | 3.12 | 0.44 | 0.03 | 8 |
| 450 | Pb 2314 | 2.58 | 0.01 | 4.68 | 2.31 | 0.45 | 10.02 |
| 450 | Pb 3024 | 2.08 | 0.01 | 4.44 | 2.87 | 0.7 | 10.1 |
| 450 | Pb 5524 | 1.89 | 0.02 | 3.58 | 2.71 | 0.73 | 8.93 |
| 450 | Pd 2314 | 4.03 | 0 | 1.58 | 0.14 | 0 | 5.76 |
| 450 | Sr 2314 | 3.71 | 0 | 4.78 | 1.68 | 0.21 | 10.39 |
| 450 | Sr 3024 | 2.51 | 0.01 | 3.76 | 1.61 | 0.26 | 8.14 |

EXAMPLE 5

Hydrodehalogenation of Bromobenzene, and Catalyst Regeneration

A test solution (1.5 ml/hr), which includes 1.9 wt % bromobenzene (PhBr) dissolved in dodecane, diluted by $N_2$ (1.1 ml/min) was fed into a tubular quartz reactor in which 3.6 g of highly dispersed precious metal catalyst ($Pd/Al_2O_3$, 0.5 wt %) was loaded. The reaction was carried out at 325° C. with a residence time of 15 s. The reaction effluent was trapped in a bubbler with 8 ml 4M NaOH solution pre-added. The carrier gas as well as the gaseous product were collected in a gas bag. All of the carbon-based products in the gas phase and oil phase in the liquid product were subjected to GC analysis. For the base trap solution, the HBr concentration was measured with an ion-selective electrode. Based on all of these measurements, carbon and bromine balances were calculated.

Figure 8:
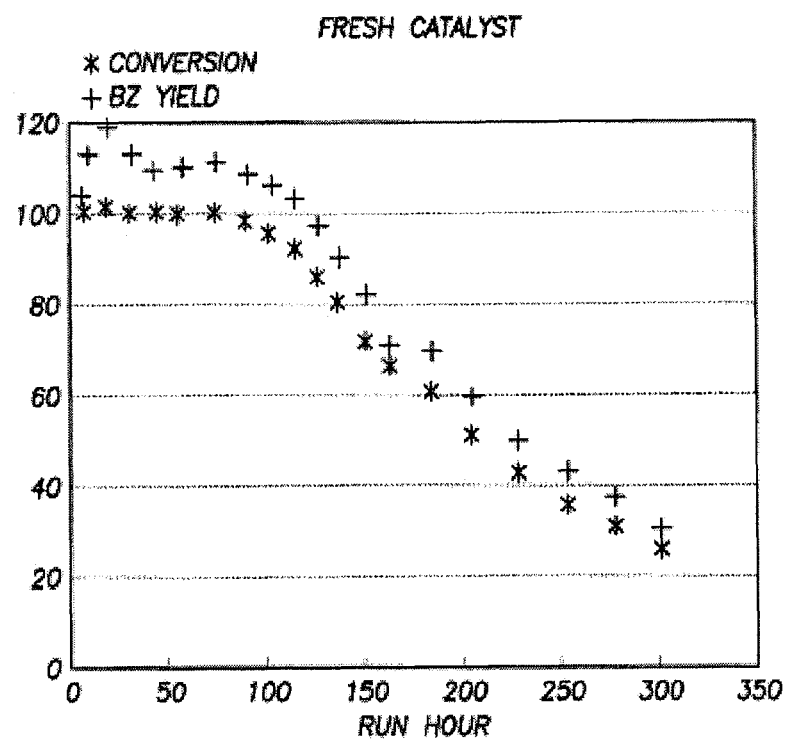
FIG. 8 is a graph of bromobenzene conversion and benzene yield as a function of time, for an experiment conducted according to one embodiment of the invention.
Figure 9:
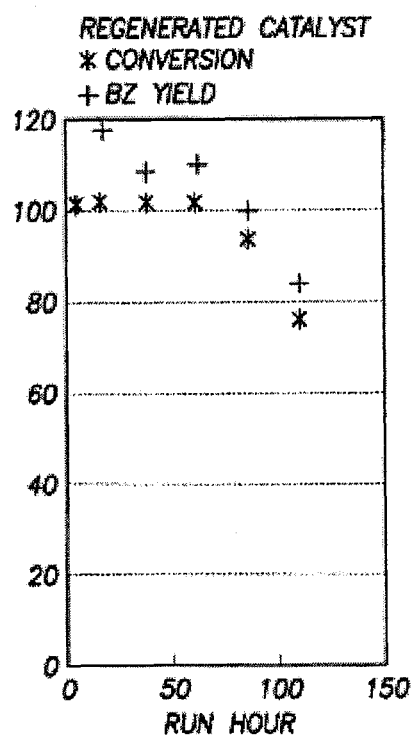
FIG. 9 is a graph of catalyst effectiveness as a function of time, for an experiment conducted according to one embodiment of the invention.

The experiment was continuously run for over 300 hours until the conversion of PhBr dropped from 100% in the initial 70 hrs to below 30% (FIG. 8). Hydrodebromination of PhBr took place over the catalyst bed with the formation of benzene ("BZ") and HBr as the major products, accompanied with some light hydrocarbons ($C_3$-$C_7$) being detected as byproducts, which originated from solvent decomposition. Carbon deposition was recognized as the primary reason for deactivation of the catalyst. The catalyst proved to be re-generable via decoking at 500° C. with $O_2$ oxidation (5 ml/min) for 10 hrs, followed by $H_2$ reduction (20 ml/min) at 400° C. for 3 hrs. The regenerated catalyst was identified to be as effective as the fresh catalyst, as confirmed by its ability to catalyze the same hydrodebromination reaction without activity loss in the first 70 hours (FIG. 9).

The invention has been described with references to various examples and preferred embodiments, but is not limited thereto. Other modifications and equivalent arrangements, apparent to a skilled person upon consideration of this disclosure, are also included within the scope of the invention. For example, in an alternate embodiment of the invention, the products 25 from the bromine generation reactor are fed directly into the bromination reactor 3. The advantage of such a configuration is in eliminating the bromine holdup needed in the flash unit 27, thereby reducing the handling of liquid bromine. Also, by eliminating the bromine scavenging section including units 26, 27, 31 and 34, the capital cost for the process can be reduced significantly. For energy efficiency, it is desirable to have the outlet of bromine generation be equal to the bromination temperature. For bromine generation, cerium-based catalysts are therefore preferred over copper-based catalysts in this embodiment, since cerium bromide has a higher melting point (722° C.) than copper (I) bromide (504° C.). The presence of oxygen in bromination and coupling reduces the selectivity to the desired products; therefore, the bromine generation reactor must consume all of the oxygen in the feed. In this embodiment, the monobromide separation 5 must be modified to remove water using a liquid-liquid split on the bottoms stream of the distillation column 51. The water removed in the liquid-liquid split contains HBr, which can be removed from water using extractive distillation (see, e.g., FIG. 5), and then recycled back to the bromine generation section.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an", as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

What is claimed is:
1. A system for forming hydrocarbons comprising:
a halogenation reactor, wherein the halogenation reactor receives a quantity of halogen and a first quantity of alkane and produces a halogenated product;
a reproportionation reactor, wherein the reproportionation reactor receives the halogenated product and a second quantity of alkane and produces at least some alkyl monohalide and a first quantity of hydrogen halide;
an oligomerization reactor comprising an oligomerization catalyst, wherein the oligomerization reactor receives alkyl monohalide and produces a quantity of hydrocarbon product and a second quantity of hydrogen halide;

a separator, wherein the separator receives the quantity of hydrocarbon product, the first quantity of hydrogen halide, and the second quantity of hydrogen halide and produces an acid stream comprising substantially all of the hydrogen halide and a gas stream comprising substantially all of the hydrocarbon product; and an oxidation reactor, wherein the oxidation reactor receives the acid stream and a source of oxygen and produces at least a quantity of halogen.

2. The system of claim 1 wherein the halogenation reactor is located in a first zone of a reactor vessel and the reproportionation reactor is located in a second zone of the reactor vessel.

3. The system of claim 2 wherein the first zone is located upstream of the second zone.

4. The system of claim 1 wherein the halogenation reactor contains a halogenation catalyst.

5. The system of claim 4 wherein the halogenation catalyst comprises at least one catalyst selected from the group consisting of: a zeolite, an amorphous alumino-silicate, an acidic zirconia, a tungstate, a solid phosphoric acid, a metal oxide, a mixed metal oxide, a metal halide, and a mixed metal halide.

6. The system of claim 1 wherein at least one of the halogenation reactor, the reproportionation reactor, and the oligomerization reactor comprises at least one material of construction selected from the group consisting of: Au, Co, Cr, Fe, Nb, Ni, Pt, Ta, Ti, Zr, and an alloy thereof.

7. The system of claim 1 wherein at least one of the halogenation reactor, the reproportionation reactor, and the oligomerization reactor comprises a fixed bed reactor or a fluidized bed reactor.

8. A system for forming hydrocarbons comprising:
a halogenation reactor, wherein the halogenation reactor receives a quantity of halogen and a first quantity of alkane and produces a halogenated product;
a reproportionation reactor, wherein the reproportionation reactor receives the halogenated product and a second quantity of alkane and produces at least some alkyl monohalide and a first quantity of hydrogen halide; and
an oligomerization reactor comprising an oligomerization catalyst, wherein the oligomerization reactor receives alkyl monohalide and produces a quantity of hydrocarbon product and a second quantity of hydrogen halide;
a separator, wherein the separator receives the quantity of hydrocarbon product, the first quantity of hydrogen halide, and the second quantity of hydrogen halide and produces an acid stream comprising substantially all of the hydrogen halide and a gas stream comprising substantially all of the hydrocarbon product;
an oxidation reactor, wherein the oxidation reactor receives the acid stream and a source of oxygen and produces at least a quantity of halogen; and
a dehydrohalogenation reactor comprising a dehydrohalogenation catalyst, wherein the dehydrohalogenation reactor receives the gas stream containing substantially all of the hydrocarbon product and produces a dehalogenated gas stream and a third quantity of hydrogen halide.

9. The system of claim 8 wherein the halogenation reactor is located in a first zone of a reactor vessel and the reproportionation reactor is located in a second zone of the reactor vessel.

10. The system of claim 8 wherein the first zone is located upstream of the second zone.

11. The system of claim 8 wherein the halogenation reactor contains a halogenation catalyst.

12. The system of claim 11 wherein the halogenation catalyst comprises at least one catalyst selected from the group consisting of: a zeolite, an amorphous alumino-silicate, an acidic zirconia, a tungstate, a solid phosphoric acid, a metal oxide, a mixed metal oxide, a metal halide, and a mixed metal halide.

* * * * *